(12) United States Patent
Waterhouse et al.

(10) Patent No.: US 11,986,385 B2
(45) Date of Patent: May 21, 2024

(54) PROTECTIVE LENS HOLDER

(71) Applicant: AcuFocus, Inc., Bridgewater, NJ (US)

(72) Inventors: Alan Waterhouse, San Diego, CA (US); R. Kyle Webb, Carlsbad, CA (US)

(73) Assignee: AcuFocus, Inc., Bridgewater, NJ (US)

( * ) Notice: Subject to any disclaimer, the term of this patent is extended or adjusted under 35 U.S.C. 154(b) by 41 days.

(21) Appl. No.: 17/807,548

(22) Filed: Jun. 17, 2022

(65) Prior Publication Data

US 2022/0387170 A1 Dec. 8, 2022

Related U.S. Application Data

(63) Continuation of application No. 16/628,533, filed as application No. PCT/US2018/040711 on Jul. 3, 2018, now Pat. No. 11,395,732.

(60) Provisional application No. 62/528,891, filed on Jul. 5, 2017.

(51) Int. Cl.
*A61F 2/16* (2006.01)
*A45C 11/00* (2006.01)

(52) U.S. Cl.
CPC .......... *A61F 2/1691* (2013.01); *A45C 11/005* (2013.01); *A61F 2002/1683* (2013.01); *A61F 2002/169* (2015.04); *A61F 2002/16902* (2015.04); *A61F 2220/0033* (2013.01)

(58) Field of Classification Search
CPC .............. A61F 2/1691; A61F 2002/169; A61F 2002/16902
See application file for complete search history.

(56) References Cited

U.S. PATENT DOCUMENTS

| | | | |
|---|---|---|---|
| 4,402,396 A | 9/1983 | Graham | |
| 4,856,234 A | 8/1989 | Goins | |
| 4,878,910 A * | 11/1989 | Koziol | A61F 2/1613 623/6.38 |
| 6,063,118 A | 5/2000 | Nagamoto | |
| 6,142,999 A | 11/2000 | Brady et al. | |
| 6,360,883 B1 | 3/2002 | Haq et al. | |
| 6,401,916 B2 | 6/2002 | Sakanishi | |
| 6,469,844 B1 | 10/2002 | Iwase et al. | |

(Continued)

FOREIGN PATENT DOCUMENTS

| | | |
|---|---|---|
| CN | 100368846 | 2/2008 |
| CN | 1734305 | 2/2009 |

(Continued)

OTHER PUBLICATIONS

International Search Report and Written Opinion for PCT/US2018/040711 dated Nov. 30, 2018 in 11 pages.

*Primary Examiner* — Javier G Blanco
(74) *Attorney, Agent, or Firm* — Simpson & Simpson, PLLC

(57) ABSTRACT

The present disclosure relates to holders for protecting intraocular lenses and methods of use. The holder includes a posterior wall and an annular wall extending anteriorly from the posterior wall and having an anterior edge. An internal space is defined by the posterior wall and the annular wall. The internal space is sized to receive a lens body of the intraocular lens. The holder also includes a locking feature configured to secure the intraocular lens. At least a portion of the locking feature is anterior to the intraocular lens when positioned in the holder.

6 Claims, 9 Drawing Sheets

(56) References Cited

U.S. PATENT DOCUMENTS

| | | |
|---|---|---|
| 6,480,346 B2 | 11/2002 | Funakoshi |
| 6,612,907 B2 | 9/2003 | Ayyagari et al. |
| 6,622,855 B1 | 9/2003 | Callahan et al. |
| 6,634,931 B2 | 10/2003 | Ayyagari et al. |
| 6,648,741 B2 | 11/2003 | Schneider |
| 6,729,939 B2 | 5/2004 | Wrue |
| 6,786,911 B2 | 9/2004 | Mitomo et al. |
| 6,866,563 B2 | 3/2005 | Green |
| 6,908,363 B2 | 6/2005 | Green |
| 6,976,584 B2 | 12/2005 | Maiola et al. |
| 7,037,338 B2 | 5/2006 | Nagamoto |
| 7,281,699 B2 | 10/2007 | Hovey et al. |
| 7,289,282 B2 | 10/2007 | Matsushima |
| 7,462,193 B2 | 12/2008 | Nagamoto |
| 7,674,288 B2 | 3/2010 | Nagamoto |
| 7,815,678 B2 | 10/2010 | Ben Nun |
| 7,992,906 B2 | 8/2011 | Nigam |
| 8,857,803 B2 | 10/2014 | Schaper, Jr. et al. |
| 9,220,590 B2 | 12/2015 | Beer |
| 9,358,103 B1 * | 6/2016 | Wortz .................. A61F 2/1691 |
| 9,693,858 B2 | 7/2017 | Hildebrand et al. |
| 9,737,461 B2 | 8/2017 | Feingold |
| 11,395,732 B2 | 7/2022 | Waterhouse et al. |
| 2001/0040740 A1 | 11/2001 | Funakoshi |
| 2002/0193052 A1 | 12/2002 | Ayyagari et al. |
| 2003/0045930 A1 | 3/2003 | Nguyen |
| 2003/0114093 A1 | 6/2003 | Wrue |
| 2003/0137636 A1 | 7/2003 | Tai |
| 2003/0176918 A1 | 9/2003 | Schneider |
| 2003/0220652 A1 | 11/2003 | Israel |
| 2004/0127911 A1 | 7/2004 | Figueroa et al. |
| 2004/0220666 A1 | 11/2004 | Cumming |
| 2005/0015144 A1 | 1/2005 | Tran |
| 2005/0049606 A1 | 3/2005 | Vaquero et al. |
| 2005/0126948 A1 | 6/2005 | Maiola et al. |
| 2005/0143813 A1 | 6/2005 | Hovey et al. |
| 2006/0037871 A1 | 2/2006 | Jin et al. |
| 2006/0117919 A1 | 6/2006 | Stute |
| 2006/0178742 A1 | 8/2006 | Nagamoto |
| 2007/0260308 A1 | 11/2007 | Tran |
| 2008/0051801 A1 | 2/2008 | Hovey et al. |
| 2008/0161912 A1 | 7/2008 | Scott |
| 2011/0140333 A1 | 6/2011 | Schaper et al. |
| 2017/0049560 A1 | 2/2017 | Cherne |
| 2017/0119521 A1 | 5/2017 | Kahook et al. |

FOREIGN PATENT DOCUMENTS

| | | |
|---|---|---|
| EP | 1515669 B1 | 6/2013 |
| WO | WO 02/016077 | 2/2002 |
| WO | WO 2005/023154 | 3/2005 |
| WO | WO 2019/010178 | 1/2019 |

* cited by examiner

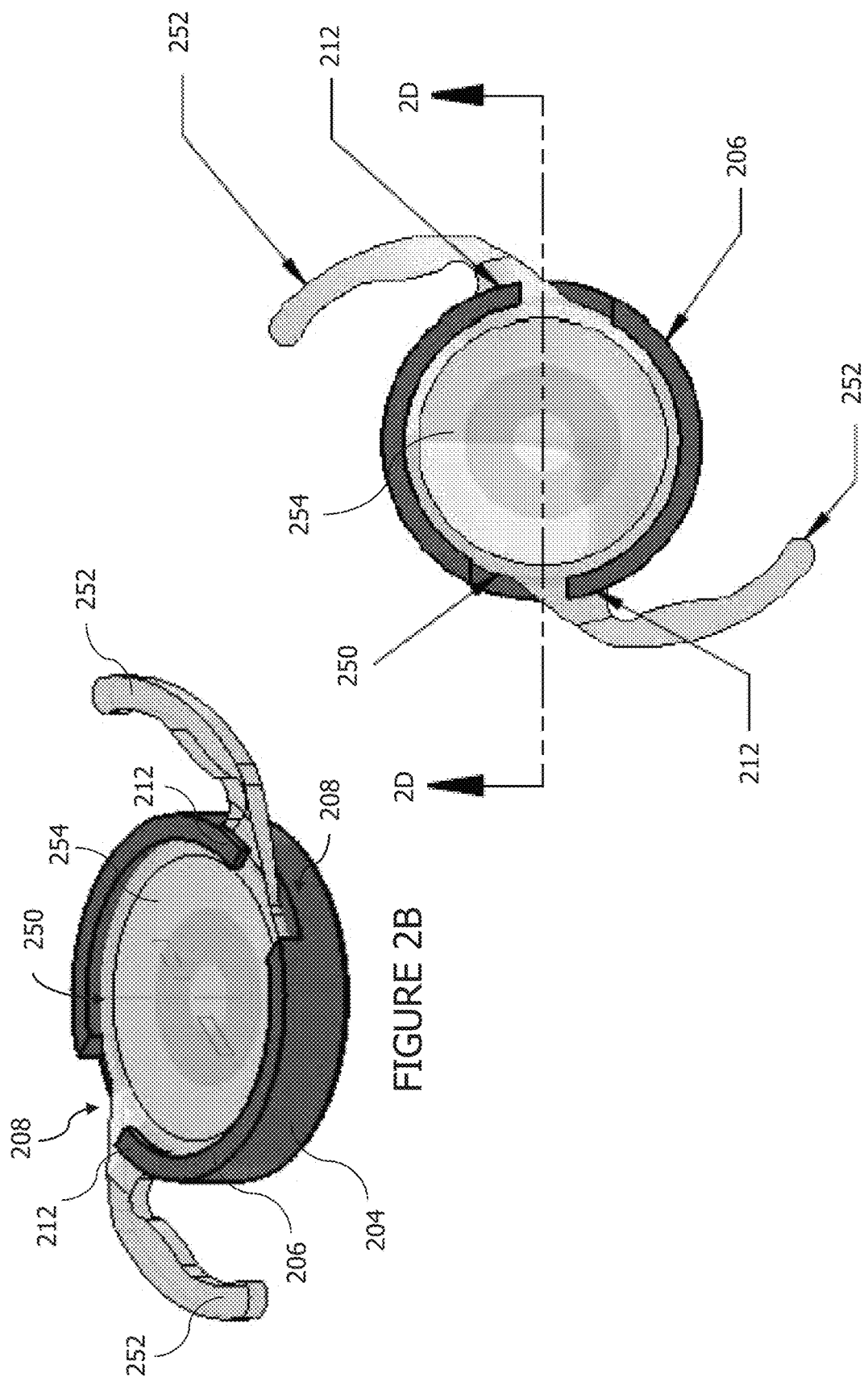

PROTECTIVE LENS HOLDER

BACKGROUND

Field

The present disclosure relates to a protective lens holder.

Description of the Related Art

An intraocular lens (IOL) is a lens implanted in the eye as part of a treatment for cataracts or myopia. IOLs usually include a lens and haptics to hold the lens in place within the capsular bag inside the eye.

SUMMARY

Intraocular lenses can be formed from universal blanks, which can be machined to a specific dioptric power. One method of finishing the lens is to cryofreeze the blank to make the material stiffer. The stiffened blank is then milled to form the shape of the lens body and/or the haptics. A surface of the lens body (e.g., anterior surface) can be lathed to create the dioptric power. After the intraocular lens is formed, the lens body can be polished (e.g., tumble polished) to remove marks from the milling and/or lathing procedures to improve image quality. In some implementations of this method, one surface of the lens body (e.g., posterior surface) and/or the periphery of the lens body does not need to be machined or polished.

The present disclosure is directed toward lens holders for protecting the surfaces and/or edges of the lens body that do not need to be machined or polished and methods of use. The lens holder provides a protective cap around the perimeter of the lens body and one surface of the lens body, while the other surface of the lens body remains exposed for polishing. The lens holder preserves the protected lens surface in its initially molded condition, while still enabling the other surface to be polished using current polishing methods (e.g., tumble polishing).

In some embodiments, the protective lens holder includes a posterior wall and an annular wall extending anteriorly from the posterior wall. The annular wall includes an anterior edge. The lens holder also includes a locking feature configured to secure the intraocular lens. At least a portion of the locking feature is anterior to the intraocular lens when the intraocular lens is positioned in the holder. An internal space is defined by the posterior wall and the annular wall. The internal space is sized to receive a lens body of the intraocular lens.

In use, the intraocular lens can be inserted into the protective lens holder and positioned between the posterior wall and at least a portion of the locking feature so that the portion of the locking feature is anterior of the intraocular lens.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

FIG. 2B is a perspective view of the lens holder shown in FIG. 2A with an intraocular lens.

FIG. 2C is a top view of the lens holder and intraocular lens shown in FIG. 2B.

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Figure 1A:
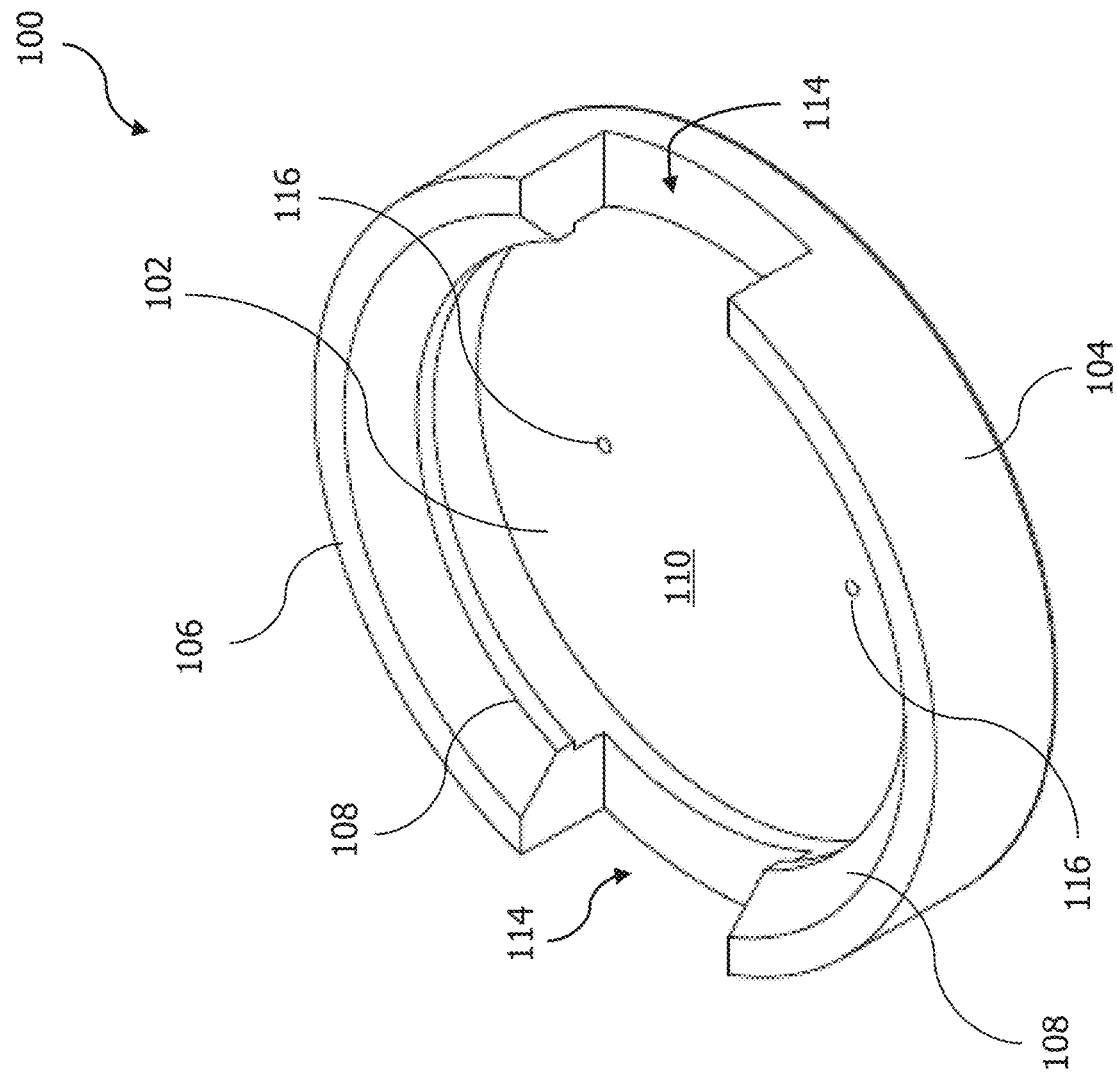
FIG. 1A is a perspective view of an embodiment of a lens holder.
Figure 1C:
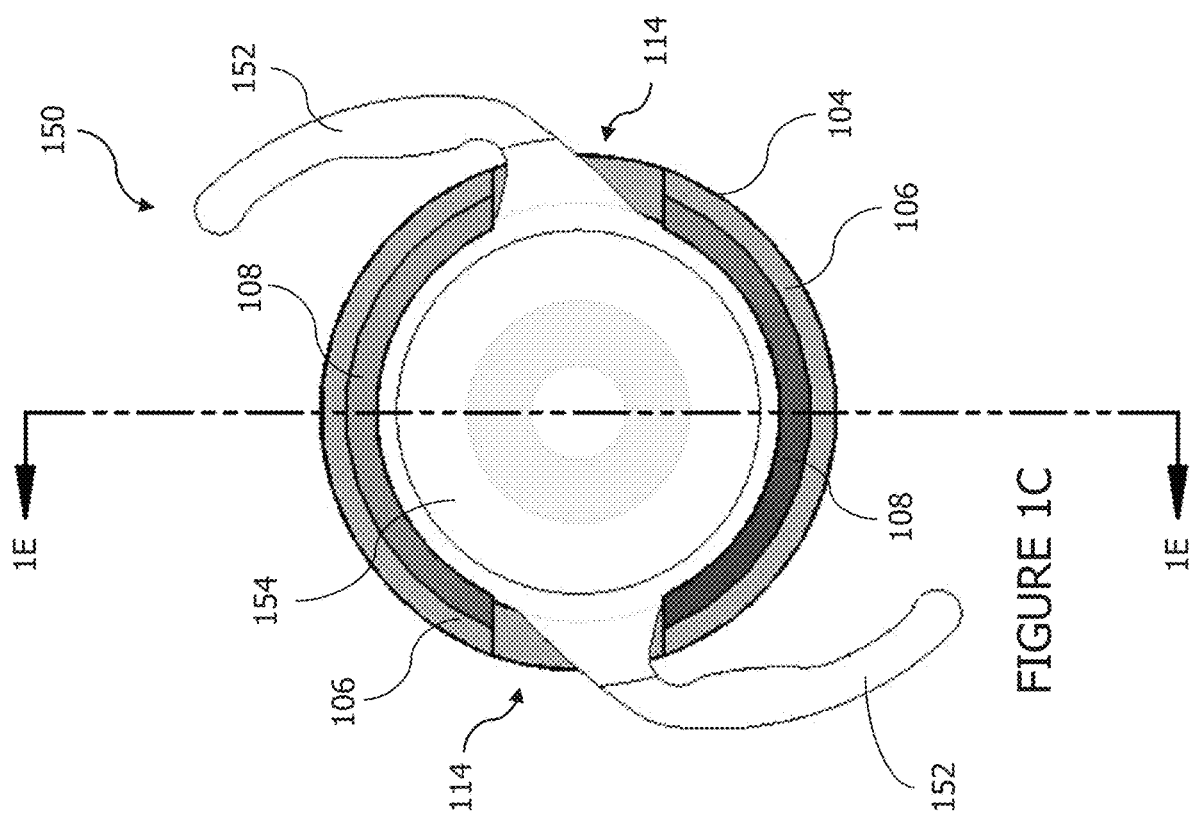
FIG. 1C is a top view of the lens holder and intraocular lens shown in FIG. 1B.
Figure 1B:
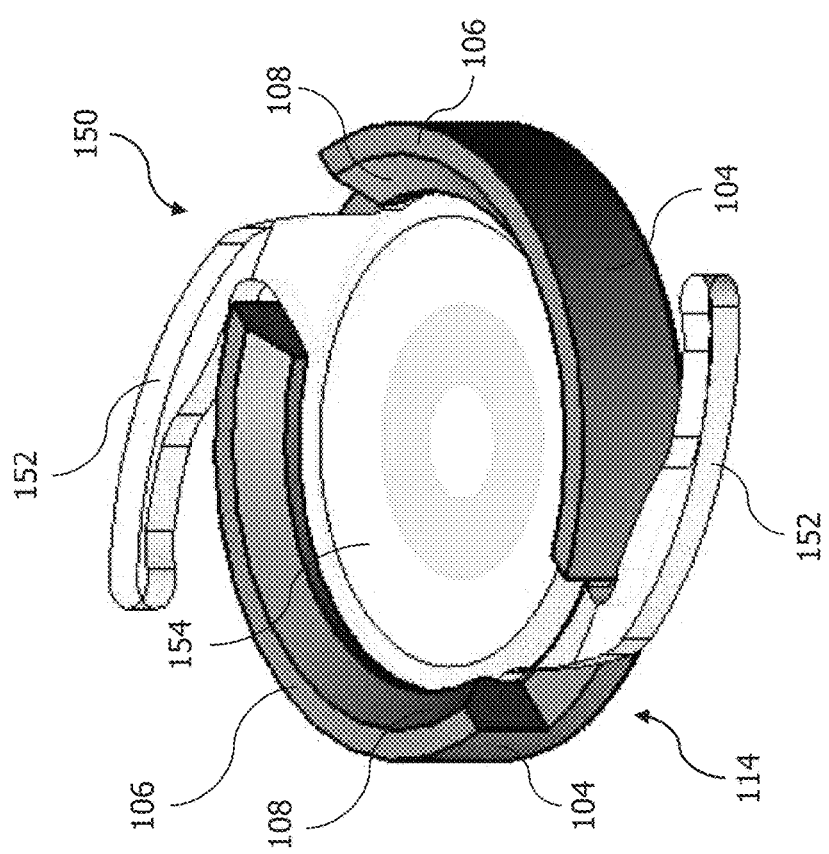
FIG. 1B is a perspective view of the lens holder shown in FIG. 1A with an intraocular lens.
Figure 1D:
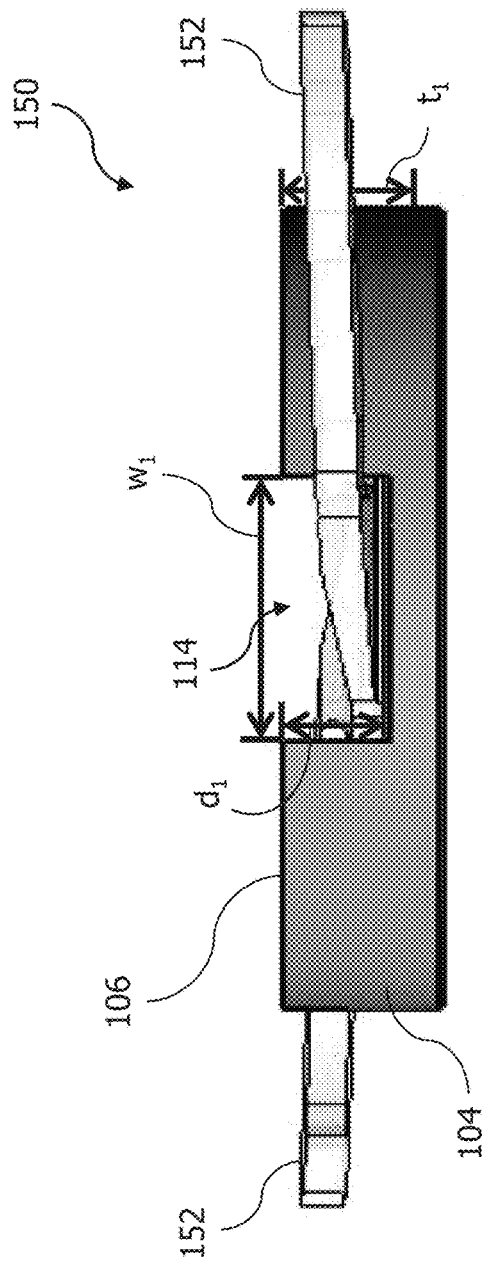
FIG. 1D is a side view of the lens holder and intraocular lens shown in FIG. 1B.

FIGS. 1A-1E illustrate a protective lens holder 100. The protective lens holder 100 includes a posterior wall 102. The lens-facing surface of the posterior wall 102 can be planar or curved. An annular wall 104 extends anteriorly from the posterior wall 102 and includes an anterior edge 106. An inner diameter of the annular wall 104 can be at least about 5.0 mm and/or less than or equal to about 7.5 mm, for example about 6.0 mm A thickness $t_1$ of an outer surface of the annular wall 104 can be at least about 1.0 mm and/or less than or equal to about 2.0 mm, for example about 1.5 mm, as shown in FIG. 1D. An internal space 110 for receiving the intraocular lens 150 is defined by the posterior wall 102 and the annular wall 104.

The lens holder 100 can include at least one recess 114 formed in the anterior edge 106 and extending at least partially through the annular wall 104. As shown in FIGS. 1A-1E, the lens holder 100 includes two recesses 114 positioned diametrically opposite each other. Each recess 114 is sized to receive a haptic 152 of the intraocular lens 150 (see FIGS. 1B and 1C). As shown in FIG. 1D, each recess 114 can have a width $w_1$ of at least about 2.0 mm and/or less about 3.0 mm, for example, about 2.5 mm Each recess 114 can have a depth $d_1$ of at least about 1.0 mm and/or less than about 2.0 mm, for example, about 1.0 mm or about 1.25 m.

The lens holder 100 includes a locking feature configured to secure the intraocular lens 150 in the lens holder 100. The locking feature includes a lip 108 extending radially inward of the annular wall 104. The lip 108 can be a discontinuous lip having two or more discrete lip portions extending radially inward from the annular wall 104.

Figure 1E:
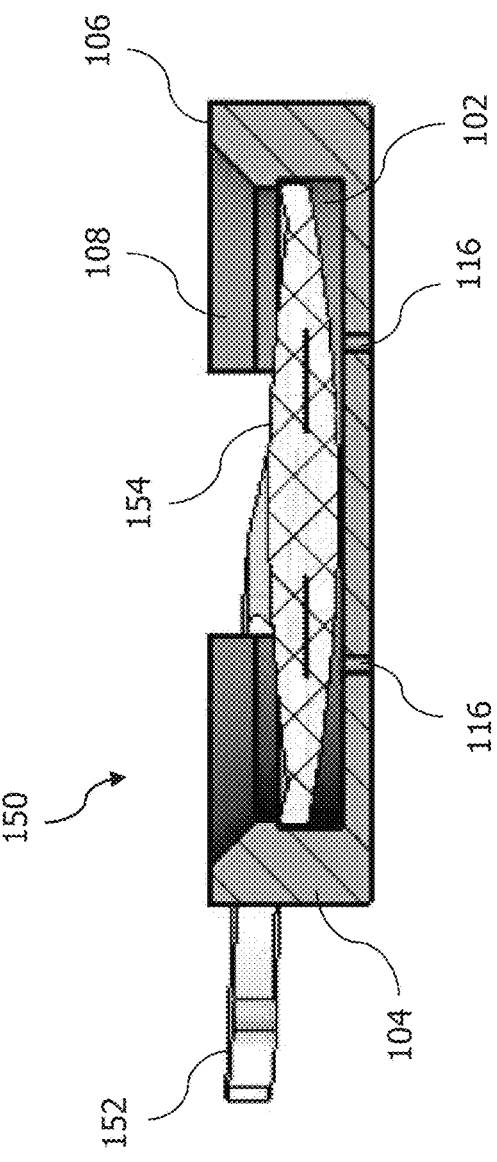
FIG. 1E is a cross-section of the lens holder and intraocular lens shown in FIG. 1C taken through line 1E-1E.

The lip 108 is spaced apart from the posterior wall 102 so that the intraocular lens 150 can be positioned in the groove or space between the lip 108 and the posterior wall 102 (see FIG. 1E). The groove or space between the lip 108 and the posterior wall 102 can have a depth, measured perpendicular to the posterior wall 102, of at least about 0.2 mm and/or less than about 0.5 mm, for example 0.25 mm or 0.27 mm. At any position, the lip 108 extends radially inward no more than about 1.0 mm (or no more than about 0.7 mm or no more than about 0.5 mm) from the annular wall 104. When the intraocular lens 150 is positioned in the holder 100, the lip 108 extends radially inward no more than about 1.0 mm (or no more than about 0.7 mm or no more than about 0.5 mm) from a periphery of the lens body 154.

As shown in the figures, the lip 108 is positioned between the anterior edge 106 of the annular wall 104 and the posterior wall 102. The anterior edge 106 can include chamfered edge extending toward the lip 108. However, in other configurations, the lip 108 could form the anterior edge 106 of the annular wall 104.

Although not shown, any edge of the lens holder 100 (e.g., the anterior edge 106, the edge between the posterior wall 102 and the annular wall 104, edges of the recess 114, and/or edges of the lip 108) can be a rounded edge. Prior to inserting the intraocular lens 150, the lens holder 100 can be tumble polished or otherwise smoothed to prevent the lens holder 100 from scratching the intraocular lens 150.

The posterior wall 102 can include at least one vent hole 116 to release air and prevent the lens holder 100 from warping the intraocular lens 150 during the polishing process. Each vent hole 116 can have a diameter of at least about 0.1 mm or at least about 0.15 m.

As shown in FIG. 1A, the lens holder 100 can include two vent holes 116. In configurations with multiple vent holes 116, each vent hole 116 can be positioned equidistant from the center of the posterior wall 102 and/or an inner surface of the annular wall 104.

The lens holder 100 can include any medical grade, biocompatible material that is sufficiently rigid and inert to withstand the polishing process. For example, the lens holder 100 can include polyetherimide (PEI), polymethyl methacrylate (PMMA), polytetrafluoroethylene (PTFE), polyoxymethylene, and/or other suitable materials.

In use, the intraocular lens 150 can be inserted into the lens holder 100 at an angle relative to the lens holder 100. A first portion of a peripheral edge of the lens body 154 can be positioned between the lip 108 and the posterior wall 102, and then a second portion of the peripheral edge of the lens body 154 can be positioned between the lip 108 and the posterior wall 102 to secure the intraocular lens 150 within the lens holder 100. Once positioned, each haptic 152 is aligned with a corresponding recess 114 (see FIGS. 1B and 1C). Also, the intraocular lens 150 can be positioned between the posterior wall 102 and at least a portion of the lip 108 so that the lip 108 is anterior of the intraocular lens 150 (see FIG. 1E).

Together, the intraocular lens 150 and the lens holder 100 undergo polishing. After polishing, which, for example, can be for a period of two to three days, the intraocular lens 150 can be removed from the lens holder 100 by grasping one of the haptics 152 (e.g., using forceps) and pulling the intraocular lens 150 out of the lens holder 100.

Figure 2A:
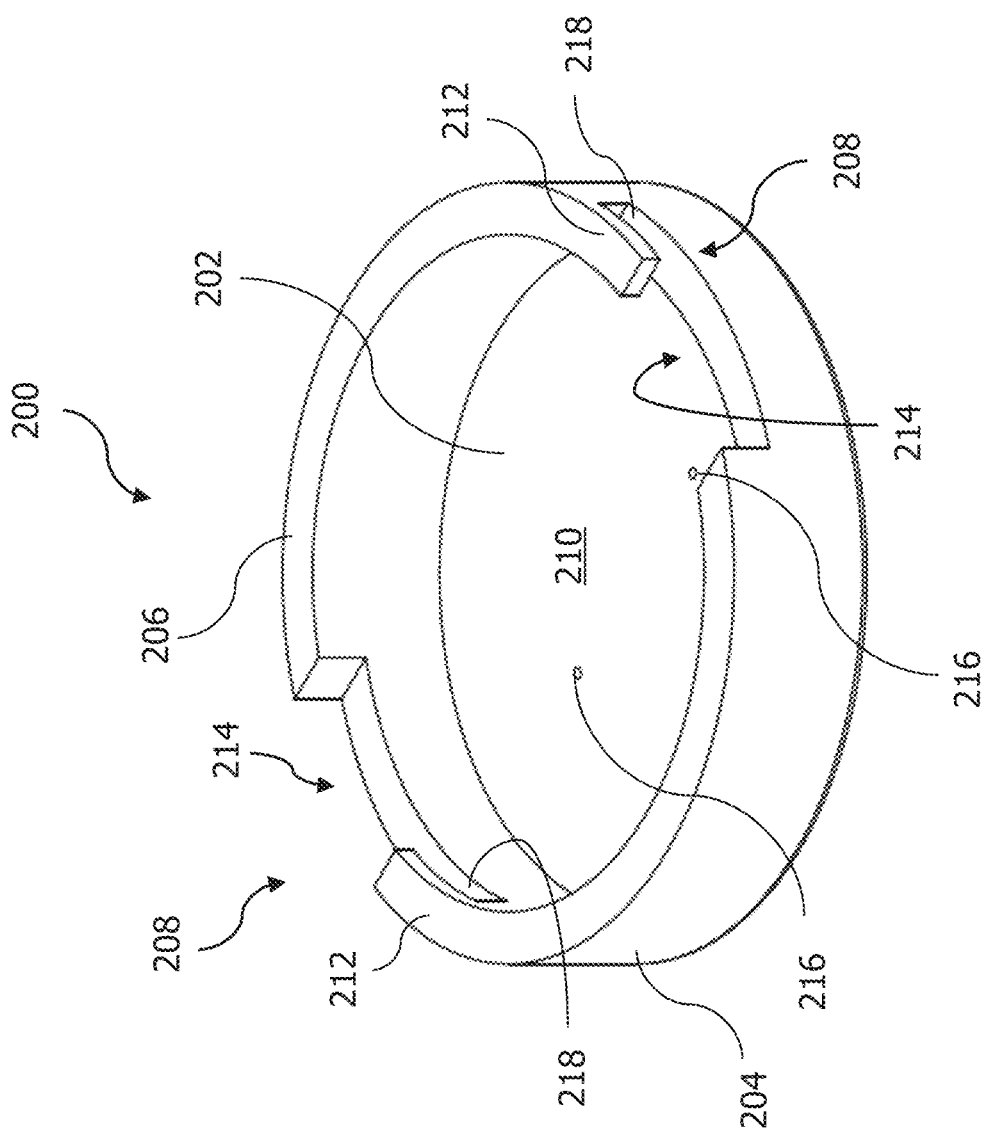
FIG. 2A is a perspective view of another embodiment of a lens holder.
Figure 2D:
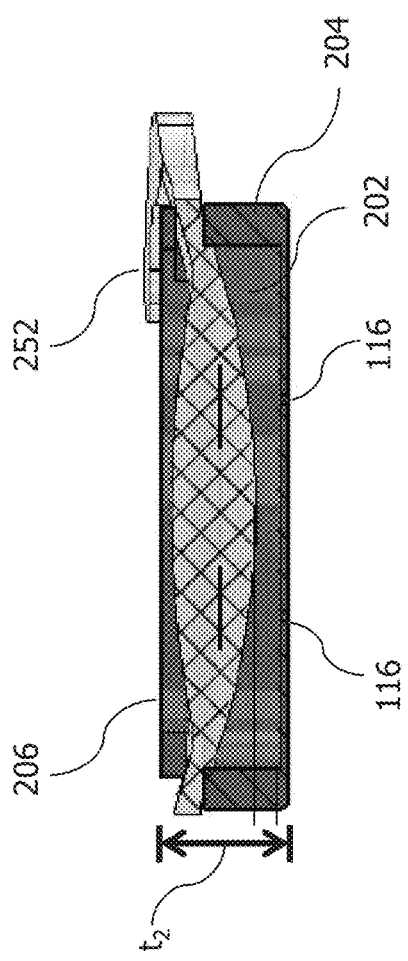
FIG. 2D is a cross-section of the lens holder and intraocular lens shown in FIG. 2C taken through line 2D-2D.

FIGS. 2A-2E illustrate another protective lens holder 200. The protective lens holder 200 includes a posterior wall 202. The lens-facing surface of the posterior wall 202 can be planar or curved. An annular wall 204 extends anteriorly from the posterior wall 202 and includes an anterior edge 206. An inner diameter of the annular wall 204 can be at least about 5.0 mm and/or less than or equal to about 7.5 mm, for example, about 6.0 mm A thickness $t_2$ of an outer surface of the annular wall 204 can be at least about 1.0 mm and/or less than or equal to about 2.0 mm, for example, about 1.5 mm, as shown in FIG. 2D. An internal space 210 is defined by the posterior wall 202 and the annular wall 204.

Figure 2E:
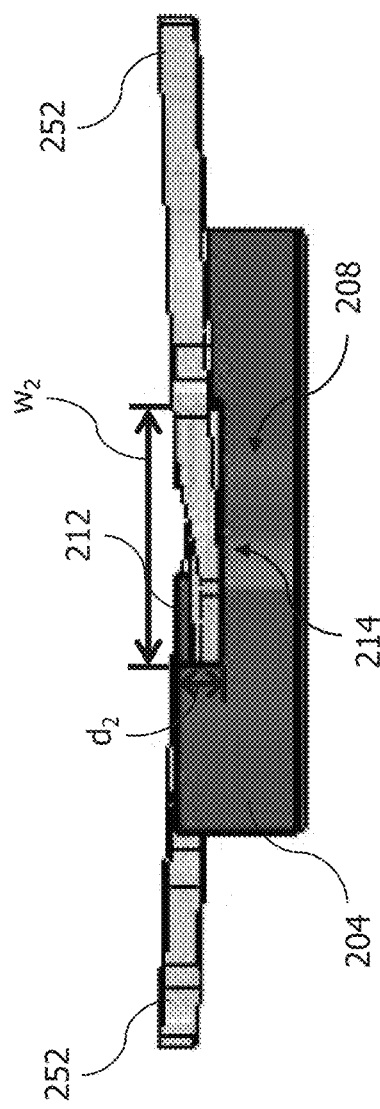
FIG. 2E is a side view of the lens holder and intraocular lens shown in FIG. 2B.

The lens holder 200 can include at least one recess 214 formed in the anterior edge 206 and extending at least partially through the annular wall 204. As shown in FIGS. 2A-2E, the lens holder 200 includes two recesses 214 positioned diametrically opposite each other. Each recess 214 is sized to receive a haptic 252 of the intraocular lens 250 (see FIGS. 2B and 2C). As shown in FIG. 2E, each recess 214 can have a width $w_2$ of at least about 2.0 mm and/or less than about 4.0 mm, for example, 3.0 mm Each recess 214 can have a depth $d_2$ of at least about 0.25 mm and/or less than 2.0 mm, for example, about 0.5 m.

The lens holder 200 includes a locking feature configured to secure the intraocular lens 250 in the lens holder 200. The locking feature can include at least one receptor 208 (e.g., a bayonet receptor). Each receptor 208 can include one of the recesses 214 and an arm 212 projecting from the annular wall 206 and across a partial width of the recess 214. A width of the arm, measured across the page in FIG. 2E, can be at least about 0.5 mm or at least about 1.0 mm, for example 1.0 m.

As shown in FIGS. 2B and 2C, each receptor 208 can secure one of the haptics 252 of the intraocular lens in the slot 218 between the arm 212 and a remainder of the annular wall 206. When the intraocular lens 250 is positioned in the lens holder 200, at least a portion of each receptor 208 (e.g., arm 212) is anterior to the intraocular lens 250. A depth of the slot 218, measured perpendicular to the posterior wall 202, can be at least about 0.2 mm, or at least about 0.3 mm, for example, about 0.315 m.

Although not shown, any edge of the lens holder 200 (e.g., the anterior edge 206, or the edge between the posterior wall 202 and the annular wall 204, edges of the recess 214, edges of the receptors 208) can be a rounded edge. Prior to inserting the intraocular lens 250, the lens holder 200 can be tumble polished to prevent the lens holder 200 from scratching the intraocular lens 250.

The posterior wall 202 can include at least one vent hole 216 to release air and prevent the intraocular lens from warping the intraocular lens 250 during the polishing process. Each vent hole 216 can have a diameter of at least about 0.1 mm or at least about 0.15 m.

As shown in FIG. 2A, the lens holder 200 includes two vent holes 216. The vent hole(s) 216. In configurations with multiple vent holes 216, each vent hole 216 can be positioned equidistant from the center of the posterior wall 202 and/or an inner surface of the annular wall 204.

The lens holder 200 can include any medical grade, biocompatible material that is sufficiently rigid and inert to withstand the polishing process. For example, the lens holder 200 can include polymethyl methacrylate (PMMA), polytetrafluoroethylene (PTFE), polyoxymethylene, and/or other suitable materials.

In use, the intraocular lens 250 can be inserted into the lens holder 200 such that each haptic 252 is aligned with a corresponding recess 254. Rotating the intraocular lens 250 in a first direction will secure each haptic 252 within a corresponding receptor 208.

Together, the intraocular lens 250 and the lens holder 200 undergo polishing. Rotating the intraocular lens 250 in a second direction, opposite the first direction, will enable removal of the intraocular lens 250 from the lens holder 200.

Figure 3A:
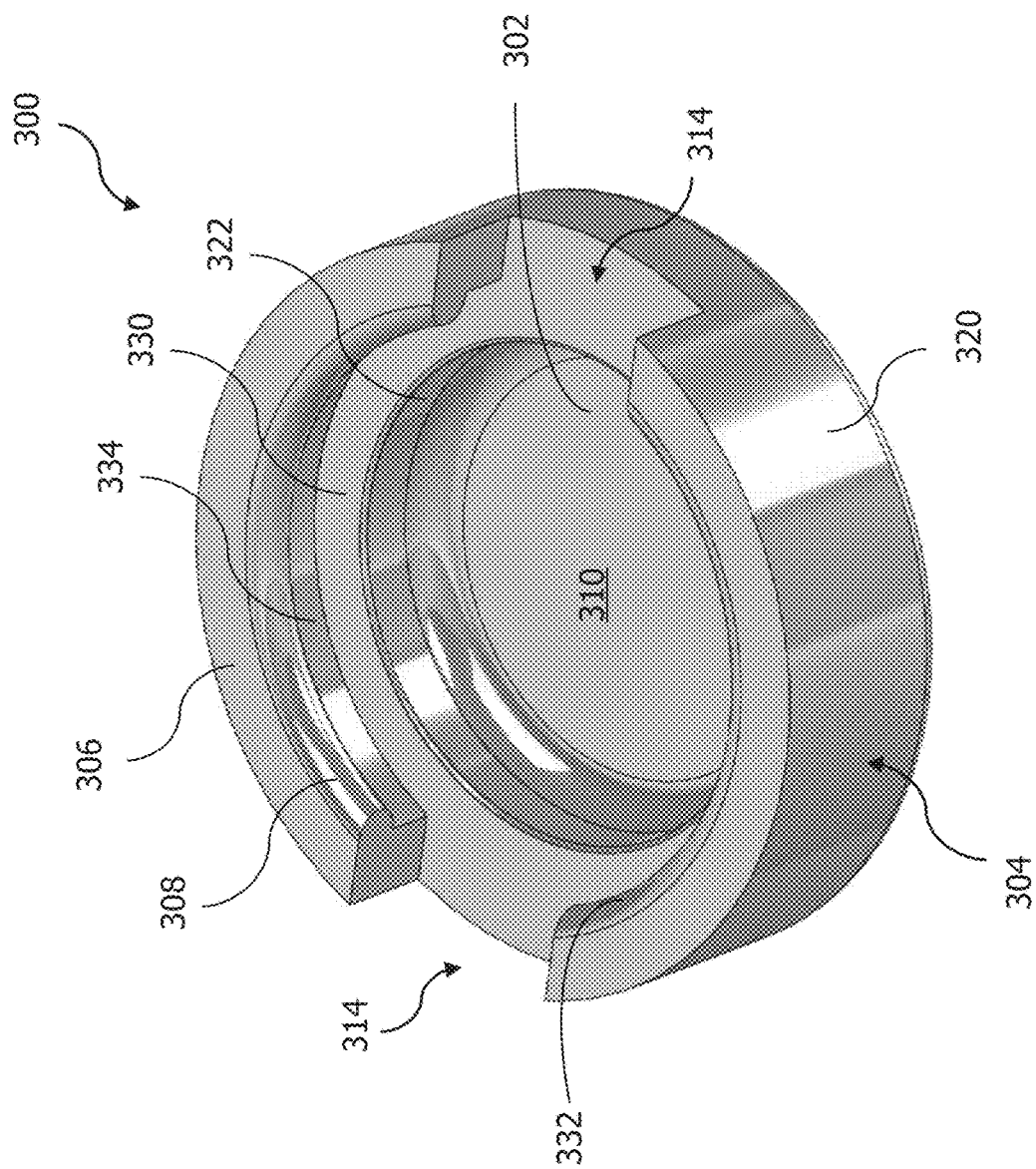
FIG. 3A is a perspective view of yet another embodiment of a lens holder.
Figure 3C:
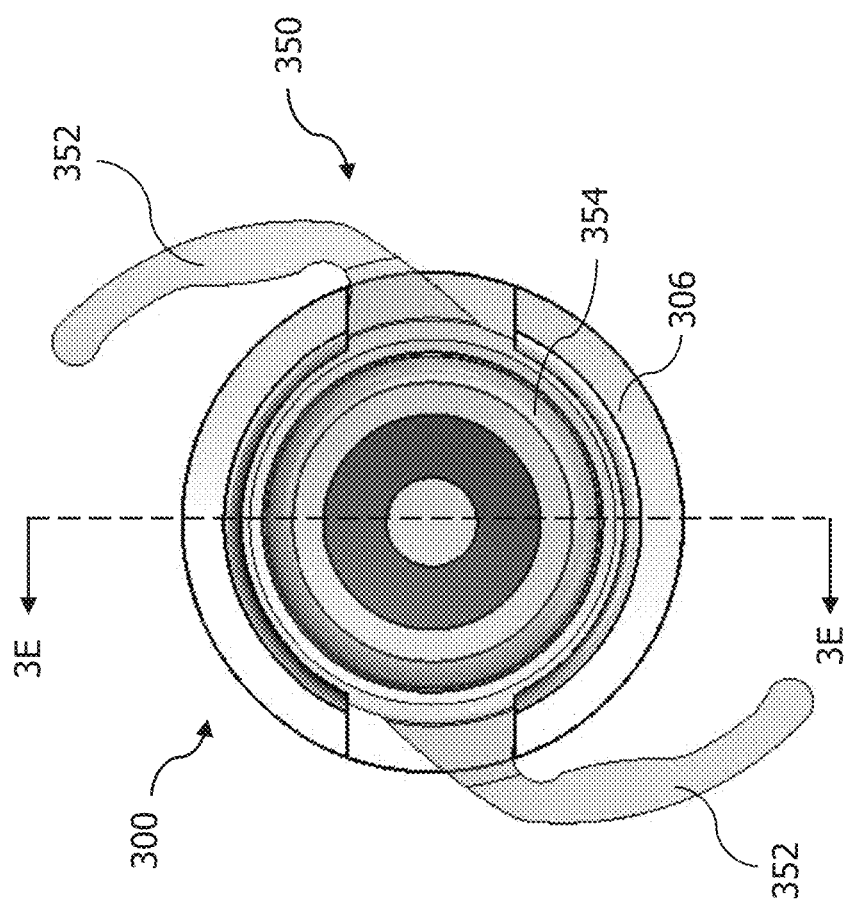
FIG. 3C is a top view of the lens holder and intraocular lens shown in FIG. 3B.
Figure 3B:
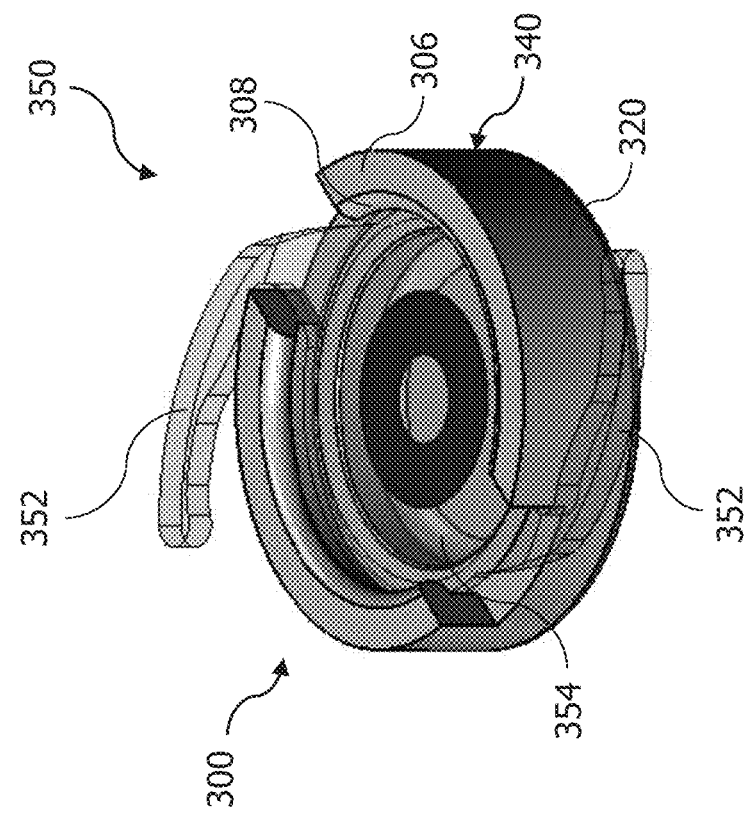
FIG. 3B is a perspective view of the lens holder shown in FIG. 3A with an intraocular lens.

FIGS. 3A-3E illustrate another protective lens holder 300. The protective lens holder 300 includes a posterior wall 302. The lens-facing surface of the posterior wall 302 can be planar or curved. An annular wall 304 extends anteriorly from the posterior wall 302 and includes an anterior edge 306. The annular wall 304 has an outer surface 320 and an inner surface 322. The inner surface 322 can have a stepped profile. For example, as shown in FIG. 3A, the inner surface 322 has a first wall portion 332, an internal ledge 330, and a second wall portion 334. The first wall portion 332 extends anteriorly from the posterior wall 302. The internal ledge 330 extends radially outward from the first wall portion 332 such that the internal ledge 330 is separated from the posterior wall 302 by the first wall portion 332. The internal ledge 330 can be parallel to the lens-facing surface of the posterior wall 302. The second wall portion 334 extends anteriorly from the internal ledge 330. The second wall portion 334 can be concentric with the first wall portion 332. The anterior edge 306 is separated from the internal ledge 330 by at least the second wall portion 334.

An internal space 310 for receiving the intraocular lens 350 is defined by the posterior wall 302 and the annular wall 304. The internal space 310 includes a first internal region 336 and a second internal region 338 anterior to the first internal region 336 (see FIG. 3E). The first internal region 336 can be defined by the lens-facing surface of the posterior wall 302 and the first wall portion 332. The second internal region 338 can be defined by the internal ledge 330 and the second wall portion 334. The first internal region 336 includes a first internal diameter $A_1$ and the second internal region 338 includes a second internal diameter $A_2$. The second internal diameter $A_2$ is at least 10% greater than the first internal diameter $A_1$, at least 20% greater than the first internal diameter $A_1$, at least 30% greater than the first internal diameter $A_1$, at least 40% greater than the first internal diameter $A_1$, or otherwise. The first internal diameter $A_1$ can be less than or equal to about 7.5 mm, less than or equal to about 6.5 mm, less than or equal to about 5.5 mm, less than or equal to about 4.5 mm or otherwise.

The first internal region 336 includes a first depth $B_1$ measured from the lens-facing surface of the posterior wall 302 to the internal ledge 330, and the second internal region 338 includes a second depth $B_2$ measured from the internal ledge 330 to the lip 308. The first depth $B_1$ can be greater than or equal to the second depth $B_2$, for example the first depth $B_1$ can be at least 1.25 times, 1.5 times, or 2.0 times second internal $B_2$. The first depth $B_1$ can be less than or equal to about 3.0 mm, less than or equal to about 2.0 mm, less than or equal to about 1.5 mm, less than or equal to about 1.0 mm, or otherwise.

Figure 3D:
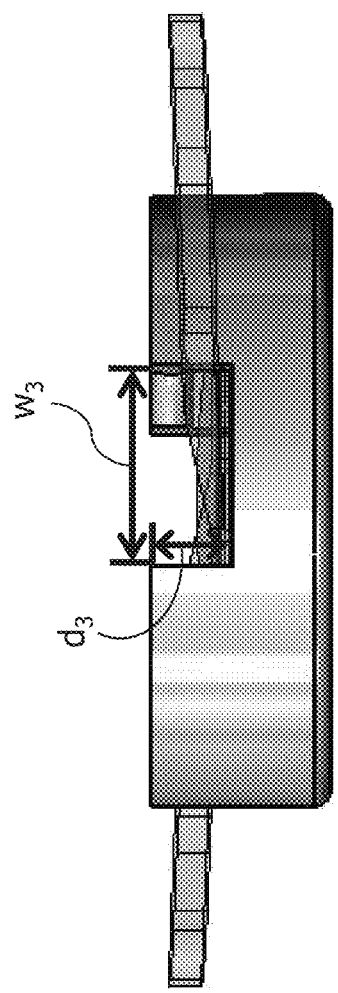
FIG. 3D is a side view of the lens holder and intraocular lens shown in FIG. 3B.

The lens holder 300 can include at least one recess 314 formed in the anterior edge 306 and extending at least partially through the annular wall 304, for example from the anterior edge 306 to the internal ledge 330. As shown in FIGS. 3A-3E, the lens holder 300 includes two recesses 314 positioned diametrically opposite each other. Each recess 314 is sized to receive a haptic 352 of the intraocular lens 350 (see FIGS. 3B and 3C). As shown in FIG. 3D, each recess 314 can have a width $w_3$ of at least about 2.0 mm and/or less about 3.0 mm, for example, about 2.5 mm Each recess 314 can have a depth $d_3$ of at least about 1.0 mm and/or less about 2.0 mm, for example, about 1.0 mm or about 1.25 m.

The lens holder 300 includes a locking feature configured to secure the intraocular lens 350 in the lens holder 300. The locking feature includes a lip 308 extending radially inward of the annular wall 304, for example at the anterior edge 306 of the annular wall 304. The lip 308 can be a discontinuous lip having two or more discrete lip portions extending radially inward from the annular wall 304. The lip 308 can include a rounded profile to avoid scratching the intraocular lens 350.

Figure 3E:
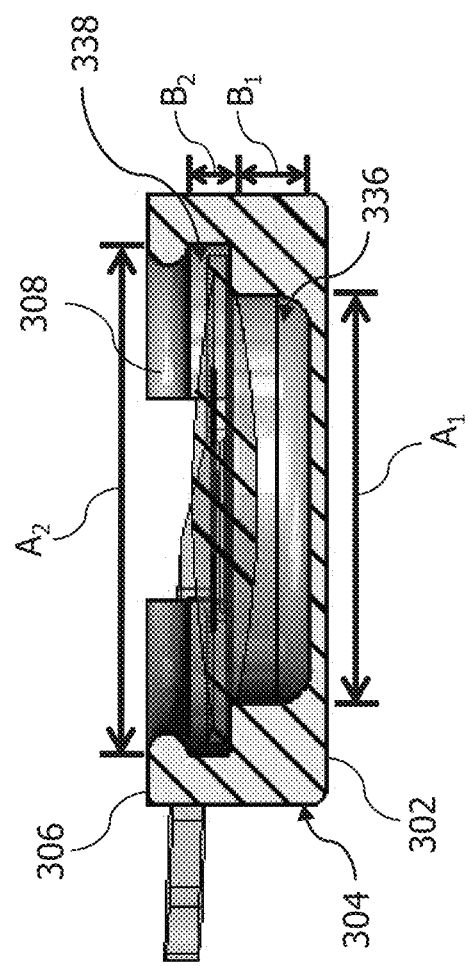
FIG. 3E is a cross-section of the lens holder and intraocular lens shown in FIG. 3C taken through line 3E-3E.

The lip 308 is spaced apart from the internal ledge 330 so that the intraocular lens 350 can be positioned in the groove or space between the lip 308 and the internal ledge 330. As shown in FIG. 3E, a periphery of the lens body 352 can be seated on internal ledge 330 such that the lens body 352 is spaced apart from the posterior wall 302 by the first internal region 336. When the intraocular lens 350 is positioned in the holder 300, the lip 308 extends radially inward no more than about 1.0 mm (or no more than about 0.7 mm or no more than about 0.5 mm) from a periphery of the lens body 354.

Similar to lens holders 100, 102, the posterior wall 302 can include at least one vent hole to release air and prevent the lens holder 300 from warping the intraocular lens 350 during the polishing process.

The lens holder 300 can include any medical grade, biocompatible material that is sufficiently rigid and inert to withstand the polishing process. For example, the lens holder 100 can include polyetherimide (PEI), polymethyl methacrylate (PMMA), polytetrafluoroethylene (PTFE), polyoxymethylene, and/or other suitable materials.

In use, the intraocular lens 350 can be inserted into the lens holder 300 at an angle relative to the lens holder 300. A first portion of a peripheral edge of the lens body 354 can be positioned between the lip 308 and the internal ledge 330, and then a second portion of the peripheral edge of the lens body 354 can be positioned between the lip 308 and the internal ledge 330 to secure the intraocular lens 350 within the lens holder 300. Once positioned, each haptic 352 is aligned with a corresponding recess 314 (see FIGS. 3B and 3C). Also, the intraocular lens 350 can be positioned between the internal ledge 330 and at least a portion of the lip 308 so that the lip 308 is anterior of the intraocular lens 350 (see FIG. 3E).

Together, the intraocular lens 350 and the lens holder 100 undergo polishing. After polishing, which, for example, can be for a period of two to three days, the intraocular lens 350 can be removed from the lens holder 300 by grasping one of the haptics 352 (e.g., using forceps) and pulling the intraocular lens 350 out of the lens holder 300.

Although the lens holders herein are described as protecting the intraocular lens during polishing, the lens holders can be used to protect the intraocular lens in other manufacturing steps and/or packaging.

Although certain embodiments and examples have been described herein, it will be understood by those skilled in the art that many aspects of the lens holders shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment.

Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "advancing the self-expanding stent" include "instructing advancing the self-expanding stent."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 1.0 mm" includes "1.0 mm" Phrases preceded by a term such as "substantially" include the recited phrase and should be interpreted based on the circumstances (e.g., as much as reasonably possible under the circumstances). For example, "substantially linear" includes "linear."

Example Embodiments

The following example embodiments identify some possible permutations of combinations of features disclosed herein, although other permutations of combinations of features are also possible.

1. A holder for protecting an intraocular lens, the holder comprising:
  a posterior wall;
  an annular wall extending anteriorly from the posterior wall, the annular wall comprising an anterior edge;
  a locking feature configured to secure the intraocular lens, at least a portion of the locking feature being anterior to the intraocular lens when positioned in the holder; and
  an internal space defined by the posterior wall and the annular wall, the internal space sized to receive a lens body of the intraocular lens.

2. The holder of Embodiment 1, further comprising at least one recess formed in the anterior edge, each recess being sized to receive a haptic of the intraocular lens.

3. The holder of Embodiment 2, wherein the at least one recess comprises two recesses positioned diametrically opposite each other.

4. The holder of any one of Embodiments 1 to 3, wherein the locking feature comprises a lip extending radially inward of the annular wall, the lip being spaced apart from the posterior wall such that the intraocular lens can be positioned between the lip and the posterior wall.

5. The holder of Embodiment 4, wherein the lip is positioned between the anterior edge of the annular wall and the posterior wall.

6. The holder of Embodiment 4 or 5, wherein at any position, the lip extends radially inward no more than about 0.7 mm from the annular wall.

7. The holder of any one of Embodiments 4 to 6, wherein the locking feature comprises a discontinuous lip extending radially inward of the annular wall.

8. The holder of any one of Embodiments 1 to 3, wherein the locking feature comprises a receptor, and wherein the receptor comprises a recess formed in the anterior edge, the recess being sized to receive a haptic of the intraocular lens.

9. The holder of any one of Embodiments 1 to 8, wherein the annular wall comprises an outer surface and an interior surface, the interior surface comprises an internal ledge positioned between the locking feature and the posterior wall.

10. The holder of any one of Embodiments 1 to 8, wherein the posterior wall comprises at least one vent hole.

11. The holder of Embodiment 9, wherein the posterior wall comprises two vent holes.

12. The holder of any one of Embodiments 1 to 10, wherein the posterior wall is planar.

13. The holder of any one of Embodiments 1 to 10, wherein the posterior wall is curved.

14. The holder of any one of Embodiments 1 to 12, wherein the holder comprises PMMA.

15. The holder of any one of Embodiments 1 to 13, wherein the anterior edge of the peripheral wall is chamfered.

16. The holder of any one of Embodiments 1 to 13, wherein the posterior wall is curved.

17. A method for protecting an intraocular lens, the method comprising:
  inserting the intraocular lens into a holder comprising:
    a posterior wall;
    an annular wall extending anteriorly from the posterior wall, the annular wall comprising a locking feature configured to secure the intraocular lens;
  positioning the intraocular lens between the posterior wall and at least a portion of the locking feature so that the portion of the locking feature is anterior of the intraocular lens.

18. The method of Embodiment 17, wherein the locking feature comprises a lip, and wherein positioning the intraocular lens comprises:

positioning a first portion of a peripheral edge of a lens body of the intraocular lens between the lip and the posterior wall; and positioning a second portion of the peripheral edge of the lens body between the lip and the posterior wall.

19. The method of Embodiment 17 or 18, wherein inserting the intraocular lens comprises inserting the intraocular lens at an angle relative to the holder.

20. The method of any one of Embodiments 17 to 19, further comprising aligning haptics of the intraocular lens with recesses in an anterior edge of the annular wall.

21. The method of Embodiment 17, wherein the locking feature comprises at least one receptor; and wherein positioning the intraocular lens comprises rotating the intraocular lens in a first direction, such that each haptic of the intraocular lens is secured with a corresponding receptor.

22. The method of Embodiment 21, further comprising rotating the intraocular lens in a second direction opposite the first direction to remove the intraocular lens from the holder.

The following is claimed:

1. An intraocular lens (IOL) holder for protecting an intraocular lens, the holder comprising:
    a posterior wall;
    an annular wall extending anteriorly from the posterior wall, the annular wall comprising an anterior edge, the annular wall having two recesses each formed in the anterior edge, the two recesses positioned opposite each other and each sized and configured to receive a corresponding haptic of the intraocular lens;
    a locking feature configured to secure the intraocular lens, at least a portion of the locking feature being anterior to the intraocular lens when positioned in the holder; and
    an internal space defined by the posterior wall and the annular wall, the internal space sized to receive a lens body of the intraocular lens,
    wherein the annular wall comprises an outer surface and an interior surface, the interior surface comprises a ledge positioned in-part between the locking feature and the posterior wall, the ledge sized and configured to receive a perimeter of an optic of the intraocular lens,
    wherein a maximum diameter of the ledge is larger than a maximum diameter of the locking feature,
    wherein the locking feature comprises a lip extending radially inward from the anterior edge, and
    wherein the posterior wall of the holder extends the entire diameter of the interior surface of the annular wall.

2. The holder of claim 1, wherein the posterior wall comprises at least one vent hole.

3. The holder of claim 2, wherein the posterior wall comprises two vent holes.

4. The holder of claim 1, wherein the posterior wall is planar.

5. The holder of claim 1, wherein the holder comprises polymethyl methacrylate.

6. The holder of claim 1, in a combination with the intraocular lens body positioned in the internal space, the intraocular lens comprising two haptics, each of the two haptics extending out of the annular wall through a corresponding one of the two recesses.

* * * * *